(12) United States Patent
Sasano et al.

(10) Patent No.: US 11,627,720 B2
(45) Date of Patent: Apr. 18, 2023

(54) ABSORBENT SHEET FOR PETS

(71) Applicant: UNICHARM CORPORATION, Ehime (JP)

(72) Inventors: Yasuhiro Sasano, Kanonji (JP); Satoshi Hasegawa, Edgewater, NJ (US); Takeshi Ikegami, Fort Lee, NJ (US)

(73) Assignee: UNICHARM CORPORATION, Ehime (JP)

( * ) Notice: Subject to any disclaimer, the term of this patent is extended or adjusted under 35 U.S.C. 154(b) by 425 days.

(21) Appl. No.: 16/622,400

(22) PCT Filed: Feb. 21, 2018

(86) PCT No.: PCT/JP2018/006305
§ 371 (c)(1),
(2) Date: Dec. 13, 2019

(87) PCT Pub. No.: WO2018/230046
PCT Pub. Date: Dec. 20, 2018

(65) Prior Publication Data
US 2020/0120894 A1  Apr. 23, 2020

(30) Foreign Application Priority Data

Jun. 15, 2017  (JP) .............................. JP2017-118115
Oct. 18, 2017  (JP) .............................. JP2017-202014

(51) Int. Cl.
*A01K 1/015*  (2006.01)
*A01K 1/01*  (2006.01)
(Continued)

(52) U.S. Cl.
CPC .......... *A01K 1/0157* (2013.01); *A01K 1/0107* (2013.01); *A61F 13/15* (2013.01);
(Continued)

(58) Field of Classification Search
CPC ................ A01K 1/0157; A01K 1/0107; Y10T 428/239; A61F 13/15
See application file for complete search history.

(56) References Cited

U.S. PATENT DOCUMENTS 6,532,897 B1 * 3/2003 Adolfsson ............ A01K 1/0125
    119/168
7,772,457 B2   8/2010 Obtsuka et al.
(Continued)

FOREIGN PATENT DOCUMENTS

CN   1644037 A    7/2005
JP   2000225145 A  8/2000
(Continued)

OTHER PUBLICATIONS

English Machine Translation of Chinese Office Action for corresponding Chinese Application No. 201880039495.5, dated Mar. 3, 2021, 7 pgs.
(Continued)

*Primary Examiner* — Alexander S Thomas
(74) *Attorney, Agent, or Firm* — Fredrikson & Byron, P.A.

(57) ABSTRACT

The absorbent sheet for pets which can suppress the spread of the excreta of a pet and can withstand the excretion action a plurality of times is provided. An absorbent sheet (10) for pets includes a topsheet (12) disposed on a top side, a backsheet (14) disposed on a back side, and an absorber (20) provided between the topsheet and the backsheet. A recess (50) is formed at least in the absorber. The recess forms a continuous line (IL) or intermittent line (IL). The line (IL) has a curved portion which does not branch.

17 Claims, 8 Drawing Sheets

(51) Int. Cl.
   *B32B 5/02* (2006.01)
   *B32B 5/26* (2006.01)
   *B32B 27/12* (2006.01)
   *A61F 13/15* (2006.01)

(52) U.S. Cl.
   CPC ............... *B32B 5/022* (2013.01); *B32B 5/26* (2013.01); *B32B 27/12* (2013.01); *B32B 2307/726* (2013.01); *B32B 2471/04* (2013.01)

(56) References Cited

U.S. PATENT DOCUMENTS

| | | | |
|---|---|---|---|
| 9,132,048 | B2 | 9/2015 | Matsushita et al. |
| 2004/0142151 | A1* | 7/2004 | Toyoshima .............. D04H 5/06 428/172 |
| 2014/0349056 | A1* | 11/2014 | Sartini ................. D21H 27/004 428/43 |

FOREIGN PATENT DOCUMENTS

| | | |
|---|---|---|
| JP | 2005152241 A | 6/2005 |
| JP | 2006238744 A | 9/2006 |
| JP | 2011205970 A | 10/2011 |
| JP | 2012213337 A | 11/2012 |
| JP | 201497241 A | 5/2014 |
| JP | 2015112268 A | 6/2015 |
| WO | 201243546 A1 | 4/2012 |

OTHER PUBLICATIONS

Untranslated Chinese Office Action for corresponding Chinese Application No. 201880039495.5, dated Mar. 3, 2021, 7 pgs.

Untranslated Office Action mailed by Chinese Patent Office for Application No. CN201880039495.5, dated May 26, 2021, 9 pages.
English Machine Translation of Office Action mailed by Chinese Patent Office for Application No. CN201880039495.5, dated May 26, 2021, 9 pages.
English Machine Translation of Notification of Reasons for Refusal mailed by Japan Patent Office (JPO) for Application No. JP2017-202014, dated May 19, 2020, 4 pages.
Untranslated Notification of Reasons for Refusal mailed by Japan Patent Office (JPO) for Application No. JP2017-202014, dated May 19, 2020, 3 pages.
PCT International Search Report dated Apr. 10, 2018 for Intl. App. No. PCT/JP2018-006305, from which the instant application is based, 4 pgs.
English Machine Translation of Japanese Publication No. 2011-205970 A, published Oct. 20, 2011, 14 pgs.
English Machine Translation of Japanese Publication No. 2000-255145 A, published Aug. 15, 2000, 28 pgs.
English Machine Translation of Japanese Publication No. 2005-152241 A, published Jun. 16, 2005, 14 pgs.
English Machine Translation of Japanese Publication No. 2014-097241 A, published May 29, 2014, 24 pgs.
English Machine Translation of Japanese Publication No. 2015-112268 A, published Jun. 22, 2015, 38 pgs.
English Abstract and Machine Translation for Chinese Publication No. CN1644037A, published Jul. 27, 2005 , 12 pgs.
English Abstract and Machine Translation for Japanese Publication No. JP2006238744A, published Sep. 14, 2006 , 22 pgs.
English Abstract and Machine Translation for Japanese Publication No. JP2012213337A, published Nov. 8, 2012 , 20 pgs.

* cited by examiner

ABSORBENT SHEET FOR PETS

RELATED APPLICATIONS

This application is a 35 U.S.C. 371 national stage filing from international application No. PCT/JP2018/006305, filed Feb. 21, 2018, which claims priority to Japanese Application No. 2017-202014, filed Oct. 18, 2017, and Japanese Application No. 2017-118115, filed Jun. 15, 2017, the teachings of which are incorporated herein by reference.

TECHNICAL FIELD

The present invention relates to an absorbent sheet for pets that absorbs pet excreta such as urine.

BACKGROUND ART

An absorbent sheet for pets for pets that absorbs pet excreta such as urine is known (see Patent Literature 1 below). The absorbent sheet for pets described in Patent Literature 1 includes a liquid-impermeable backsheet, a liquid-permeable topsheet, and an absorber positioned between the backsheet and the topsheet. The emboss processed portion which has the radial recess formed radially from the center to the edge portion is formed in the absorber.

CITATION LIST

Patent Literature

Patent Literature 1: JP 2011-205970 A

SUMMARY OF INVENTION

In Patent Literature 1, a plurality of radial recesses extends continuously and linearly in the radial direction from the center of the absorbent sheet for pets. Therefore, pet excreta, for example, urine-like liquid, diffuses linearly at the shortest distance toward the edge portion of the absorbent sheet for pets through the radial recesses. Therefore, the excreta easily diffuse to a position far from the point where the pet performs the excretion action.

As described above, Patent Literature 1 discloses an idea of diffusing excreta throughout the absorbent sheet for pets and absorbing the excreta throughout the absorbent sheet for pets. However, a pet such as dogs has the habit of not performing the excretion action again where urinary traces are visible. Therefore, when the pet excreta are diffused widely throughout the absorbent sheet for pets, the pet may not use the same Absorbent sheet for pets a plurality of times. Therefore, the user needs to replace the absorbent sheet for pets once the pet has performed the excretion action.

Therefore, an absorbent sheet for pets that suppresses the spread of pet excreta and that can withstand the excretion action of the pet a plurality of times is desired.

BRIEF DESCRIPTION OF DRAWINGS

An absorbent sheet for pets according to an embodiment includes a topsheet disposed on a top side, a backsheet disposed on a back side, and an absorber provided between the topsheet and the backsheet. A recess is formed at least in the absorber. The recess forms a continuous line or intermittent line. The line has a curved portion which does not branch.

DESCRIPTION OF EMBODIMENTS

(1) Outline of Embodiment

At least the following matters will become apparent from the description of the present specification and the accompanying drawings.

An absorbent sheet for pets according to an embodiment includes a topsheet disposed on a top side, a backsheet disposed on a back side, and an absorber provided between the topsheet and the backsheet. A recess is formed at least in the absorber. The recess forms a continuous line or intermittent line. The line has a curved portion which does not branch.

Pet excreta such as urine are likely to diffuse along the lines formed by the recesses. According to this aspect, since the line formed by the recesses has a curved portion that does not branch, the excreta does not spread linearly from the point where the pet has performed the excretion action, but spreads while turning at the curved portion. Therefore, the excreta do not spread linearly from the point where the excretion action has been performed toward the end portion, but is bent by the amount of the curved portion. As a result, the excreta can be prevented from reaching further away from the excretion point and can easily withstand the excretion action a plurality of times.

According to a preferred embodiment, a portion, of the line, along a radial direction extending outward from a center of the topsheet is bent so as to have a component along a direction intersecting the radial direction.

Since the portion along the radial direction is bent so as to have a component along the direction intersecting the radial direction of the lines formed by the recesses, it is possible to prevent the excreta from diffusing linearly toward the edge portion of the absorbent sheet for pets. As a result, the diffusion of the excreta to the edge portion of the absorbent sheet for pets can be suppressed.

According to a preferred embodiment, he recess forms an intermittent line. Since the recesses form an intermittent line, that is, the recesses are provided intermittently, the time required for excreta to move between the recesses increases. As a result, the speed of diffusion of excreta can be moderately suppressed, and excessive diffusion of excreta can be suppressed.

According to a preferred embodiment, a plurality of the recesses having different depths is arranged along the line. As a result, it takes time for excreta to move from a deep recess to a shallow recess. Therefore, the speed of diffusion of excreta along the line formed by the recesses can be moderately suppressed, and excessive diffusion of the excreta can be suppressed.

According to a preferred embodiment, the line forms a plurality of figures separated from each other. As a result, the excreta diffuse locally on the point where the excretion action is performed, or in a region of a figure close to the point and a region in its vicinity, and excessive excretion of the excreta can be suppressed.

According to a preferred embodiment, each of the figures substantially or completely encloses a region within the each figure. As a result, when the excreta reaches the point where the excretion action is performed or the top recesses that form the figure close to the point, it diffuses along a line that substantially or completely encloses a region within the figure. The excreta diffused in this way gradually diffuse from the line to the inner region and the outer region of the figure. As a result, the excreta is likely to diffuse locally on the point where the excretion action is performed, or in a region of a figure close to the point and a region in its vicinity, and excessive excretion of the excreta can be further suppressed.

According to a preferred embodiment, the recess includes a top recess that is recessed in a direction from the top side toward the back side. Since the above-mentioned recesses are top recesses that are recessed at least from the top side to the back side of the absorber, the top recesses can temporarily retain the liquid. As a result, the diffusion of the liquid to the face direction can be suppressed.

According to a preferred embodiment, the recess includes a back recess that is recessed in a direction from the back side toward the top side. Since the above-described recesses are back recesses that are recessed at least from the back side to the top side of the absorber, the back recesses can constitute a liquid reservoir. As a result, even if part of the absorbed liquid flows out from the absorber, the diffusion of the liquid in the face direction can be suppressed because it is retained by the back recesses.

According to a preferred embodiment, the recess includes a top recess that is recessed in the direction from the top side toward the back side and a back recess that is recessed in the direction from the back side toward the top side. The back recess is provided at a position same as a position of the top recess in a thickness direction.

Since excreta are easy to diffuse along the top recesses, it is easily absorbed into the absorber from the top recesses. The excreta absorbed by the absorber from the top recesses is easily retained at the back recesses provided at the same position as the top recesses in the thickness direction. As a result, the excessive diffusion of the excreta from the top recesses and the back recesses to the outside can be suppressed.

According to a preferred embodiment, a depth of the back recess is shallower than a depth of the top recess. The excreta retained at the back recesses may diffuse widely through the boundary between the absorber and the backsheet due to capillary action. According to this aspect, by making the depth of the back recesses shallower than the depth of the top recesses, it is possible to suppress the excessive amount of excreta retained at the back recesses, and as a result, it is possible to suppress the amount of excreta that spreads through the boundary between the absorber and the backsheet. As a result, the excessive diffusion of the excreta from the top recesses and the back recesses to the outside can be suppressed.

According to a preferred embodiment, the recess is formed by an embossed portion obtained by compressing the absorber. When the recess is formed by the embossed portion, the density of the absorber at the recess is higher than the density around it. Since the density of the absorber is high at the recess, the excreta are easily retained by the absorber at the recess due to capillary action. As a result, the excessive diffusion of the excreta from the recess to the outside can be suppressed.

According to a preferred embodiment, the curved portion occupies 50% or more of the entire line. Since most of the lines formed by the recesses are curved, the line connecting the two points on the absorbent sheet for pets is significantly longer than the shortest distance (linear distance). Therefore, it is possible to prevent the excreta from spreading excessively.

(2) Configuration of Absorbent Sheet for Pets

Hereinafter, the absorbent sheet for pets according to the embodiment will be described with reference to the drawings. In the following description of the drawings, the same or similar parts are denoted by the same or similar reference symbols. However, note that the drawings are schematic, and ratios of dimensions are different from actual ones. Therefore, specific dimensions and the like are determined in consideration of the following description. Moreover, there may be portions where dimensional relationships or proportions are different among the drawings.

In the present specification, "pet" broadly encompasses vertebrates and invertebrates, and typically includes pets such as cats, dogs, rabbits, and hamsters.

Figure 1:
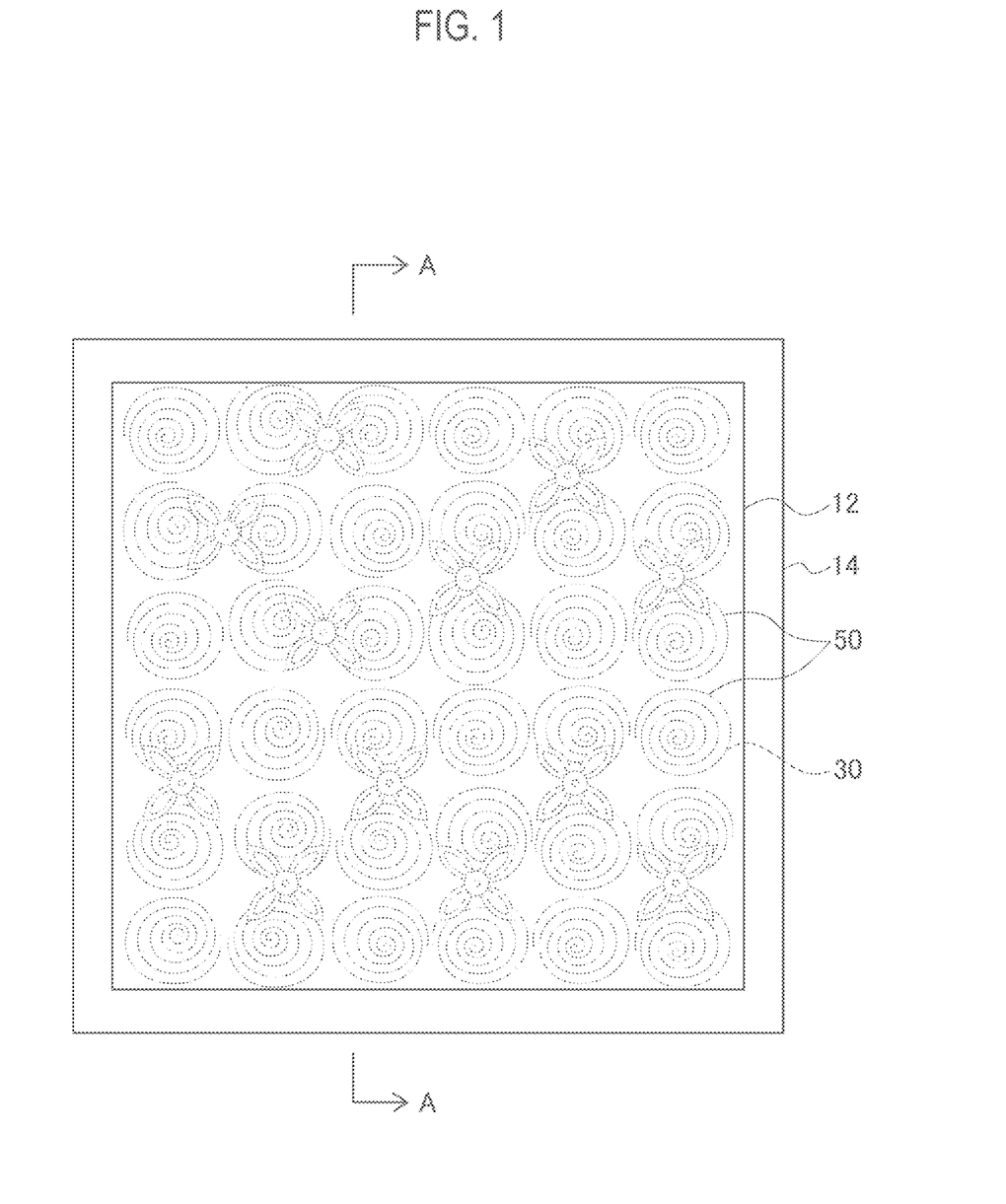
FIG. 1 is a plan view of an absorbent sheet for pets according to a first embodiment.
Figure 2:
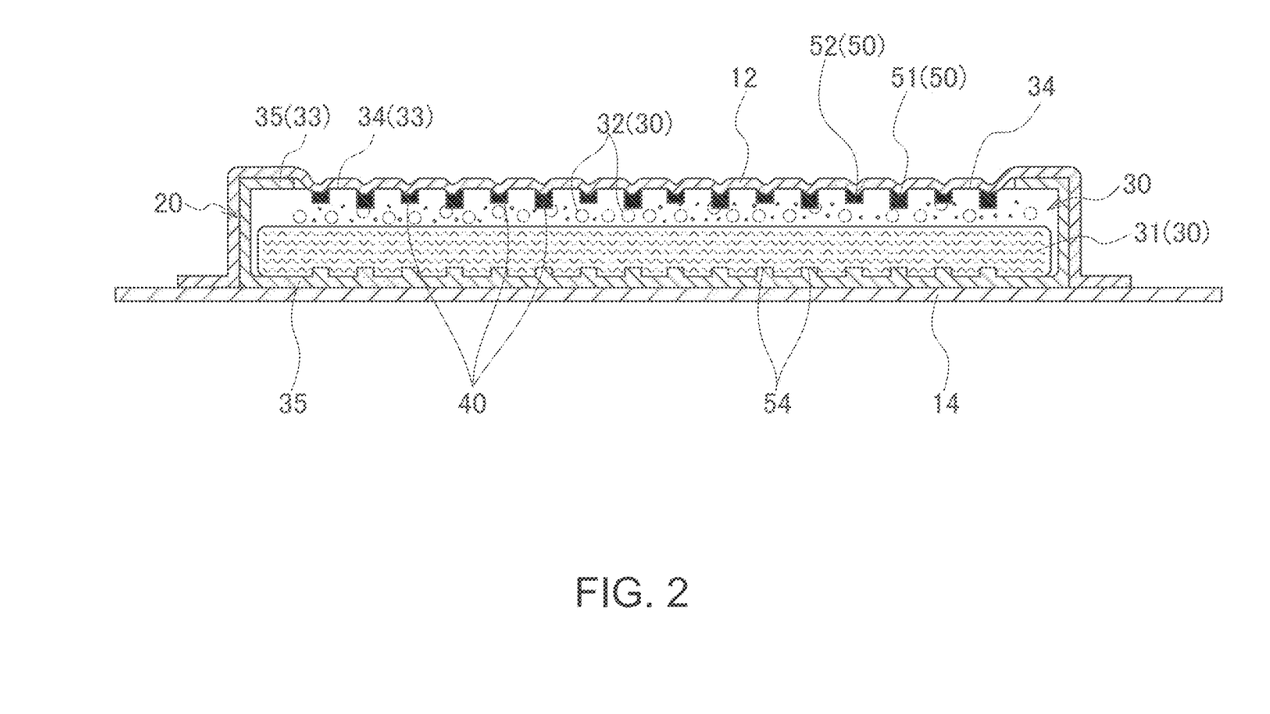
FIG. 2 is a schematic cross-sectional view of the absorbent sheet for pets taken along line A-A shown in FIG. 1.

FIG. 1 is a plan view of the absorbent sheet for pets according to the first embodiment. FIG. 2 is a schematic cross-sectional view of the absorbent sheet for pets taken along line A-A shown in FIG. 1. An absorbent sheet for pets 10 is a generally flat sheet. One face of the absorbent sheet for pets 10 is a face that receives pet excreta, and is also referred to as an "excretion face" below. FIG. 1 is a plan view of the absorbent sheet for pets as seen from the excretion face.

The absorbent sheet for pets 10 includes a topsheet 12 disposed on the top side, a backsheet 14 disposed on the back side, and an absorber 20. The absorber 20 is provided between the topsheet 12 and the backsheet 14.

The topsheet 12 may be a liquid-permeable sheet that liquid such as pet excreta permeates. The liquid-permeable sheet may be composed of, for example, a liquid-permeable nonwoven fabric or an opening film.

The backsheet 14 may be a liquid-impermeable sheet that liquid such as pet excreta does not permeate. The backsheet 14 is not particularly limited, but may be composed by, for example, a resin film sheet.

In the present embodiment, part of the backsheet 14 extends outward of the topsheet 12. Therefore, the backsheet 14 can be visually recognized from the excretion face for the outer peripheral portion of the absorbent sheet for pets 10.

The absorber 20 may include an absorbent core 30 and a core wrap 33 that wraps the absorbent core 30. The core wrap 33 may include a cover layer 34 that covers the excretion face side of the absorbent core 30, and a wrap layer 35 that covers the side face and the back face of the absorbent core 30. In this case, the absorbent core 30 is wrapped by the cover layer 34 and the wrap layer 35. The cover layer 34 and the wrap layer 35 are not particularly limited, but can be composed of, for example, a liquid-permeable tissue.

The absorbent core 30 may include, but is not limited to, a hydrophilic fiber layer 31 such as pulp, and a super absorbent polymer (SAP) 32, or a combination thereof. As an example, in the present embodiment, the super absorbent polymer (SAP) 32 is provided on the hydrophilic fiber layer 31. The hydrophilic fiber layer 31 may be wrapped with a tissue layer (not shown).

The absorbent sheet for pets 10 has a recess 50 that is recessed in a direction from the topsheet 12 toward the backsheet 14. Hereinafter, this recess 50 is referred to as a "top recess 50" for convenience. The top recess 50 may be formed at least on the absorber 20.

At least one top recess 50 may be provided on the absorber 20. In the present embodiment, a large number of dot-shaped top recesses 50 are provided. These dot-shaped top recesses 50 may be arranged so as to constitute an intermittent line IL. Alternatively, the top recesses 50 may extend linearly or curvilinearly to form a continuous line IL.

The top recess 50 may be formed by at least an embossed portion obtained by compressing the absorber 20. This embossed portion may be formed by compressing only the absorber 20, or may be formed by compressing both the absorber 20 and the topsheet 12. When the top recess 50 is formed by an embossed portion, the density of the absorber 20 at the position of the top recess 50 is higher than the density of the absorber 20 around the top recess 50.

When the top recess 50 is formed by the embossed portion, the density of the absorber 20 at the top recess 50 is higher than the density around it. Excreta are easily absorbed into the absorber 20 from the top recess 50. Since the density of the absorber 20 is high at the top recess 50, the excreta is easily retained in the absorber at the top recess 50 due to capillary action. As a result, excessive diffusion of excreta from the top recess 50 to the outside can be suppressed.

Alternatively, the top recess 50 may be configured by lowering at least the basis weight of the absorber 20. In this case, the basis weight of the absorber 20 at the position of the top recess 50 may be lower than the basis weight of the absorber 20 around the top recess 50.

The absorbent sheet for pets 10 may have a functional material 40. The functional material 40 may contain a drug, for example. The functional material 40 is provided at the position of the top recess 50. Preferably, the functional material 40 is provided closer to the absorber 20 than the topsheet 12 at the position of the top recess 50. In the present embodiment, the functional material 40 is provided on the cover layer 34 constituting the absorber 20 at the position of the top recess 50 as an example.

Figure 3:
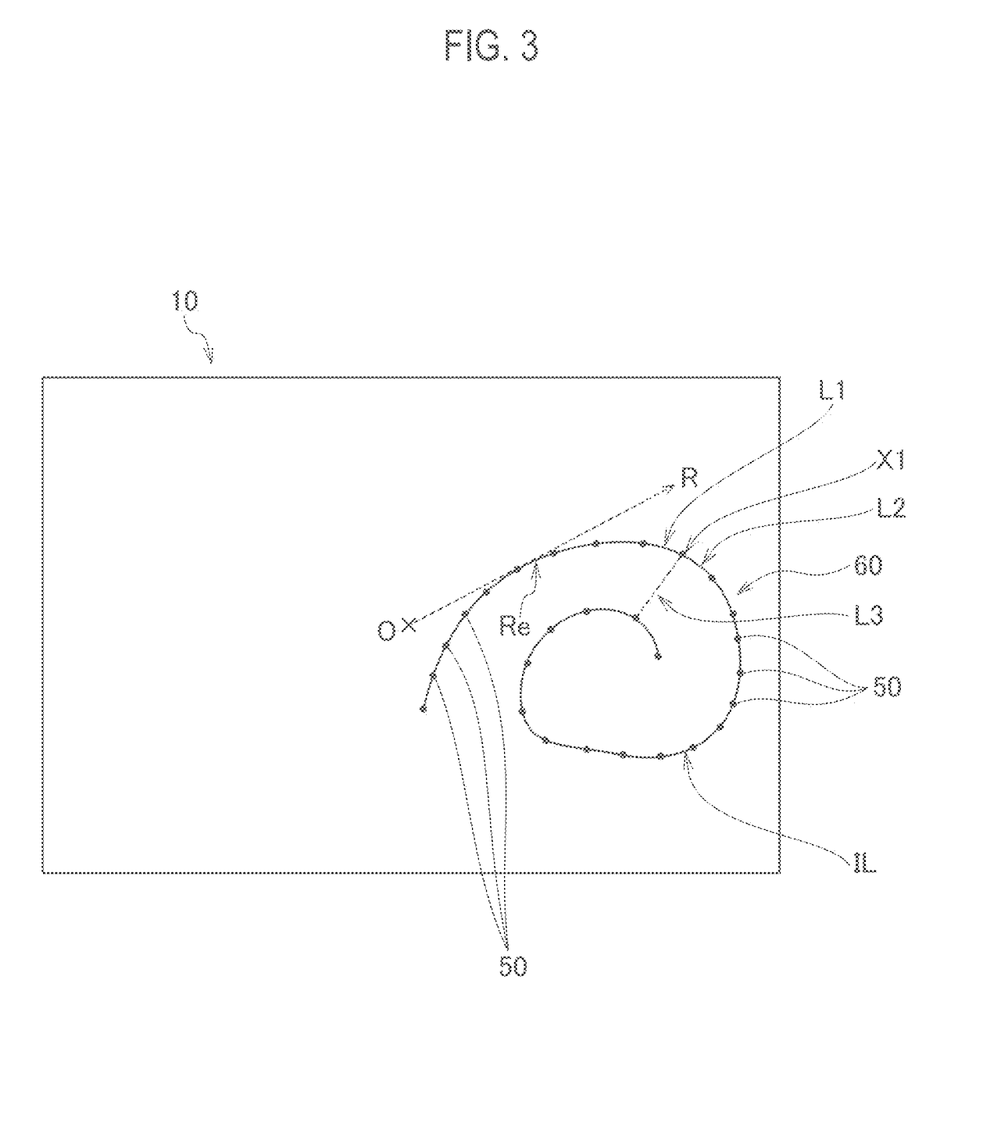
FIG. 3 is a diagram for explaining an example of a pattern of top recesses provided in the absorbent sheet for pets.

The continuous or intermittent line IL formed by the top recesses 50 will be described with reference to FIG. 3. FIG. 3 illustrates an example of a pattern of the top recesses 50 provided in the absorbent sheet for pets.

The continuous or intermittent line IL formed by the top recesses 50 has a curved portion that does not branch. That is, the line IL does not branch into a plurality of lines in the region where the line IL is bent. The "curved portion" may be a folded portion or a smoothly curved portion. The line formed by the top recesses 50 may also contain the branched curved portion.

Here, "continuous line" means that the top recesses 50 are a groove extending continuously. In addition, the "intermittent line" is defined by an imaginary line that connects the top recesses 50 that are close enough to be regarded as an "intermittent line" by the user's vision. In particular, the imaginary line is defined by a line (L1, L2 in FIG. 3) connecting a top recess 50 that exists at a position away from a specific top recess 50 by a distance not more than 1.5 times the distance between the specific top recess (for example, X1 in FIG. 3) and a top recess closest to the specific top recess X1 and the specific top recess 50. Therefore, a line (for example, L3 in FIG. 3) connecting top recesses 50 away from each other by a distance longer than 1.5 times the distance between the specific top recess X1 and a top recess closest to the specific top recess X1 is not configured as the intermittent line IL (imaginary line). Further, as an example, the imaginary line may be defined by a line connecting the top recesses 50 having an interval of 1 cm or less, more preferably 5 mm or less therebetween.

Figure 4:
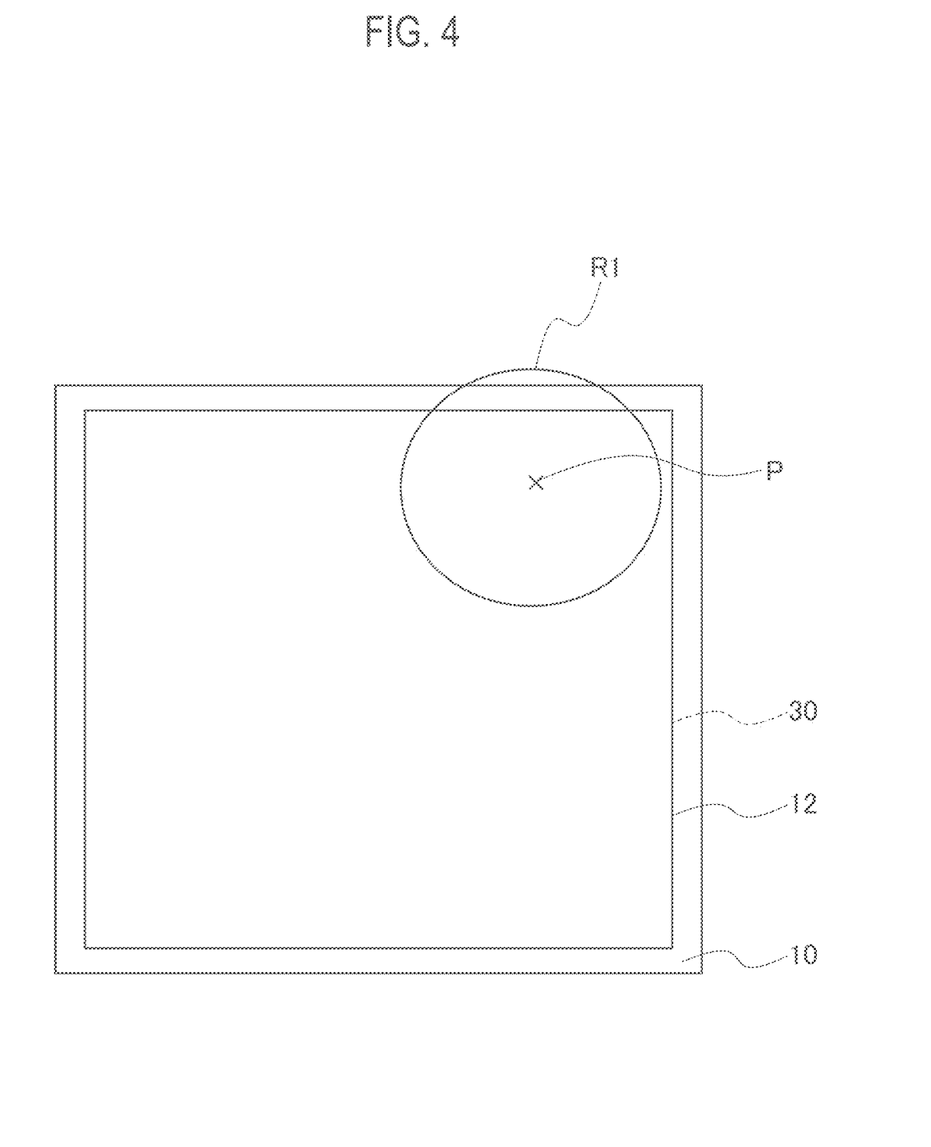
FIG. 4 is a diagram for explaining the spread of excreta in the absorbent sheet for pets having no recess.
Figure 5:
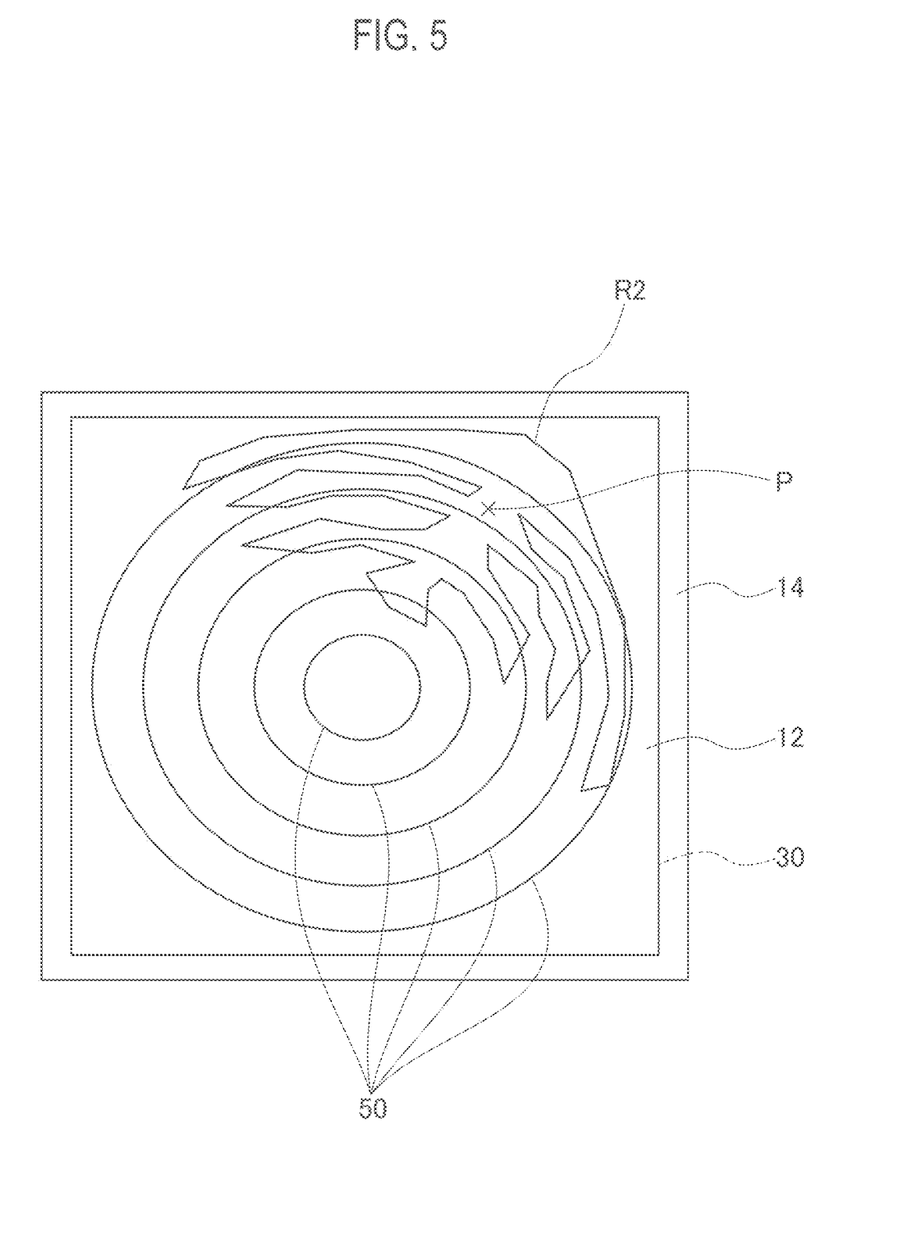
FIG. 5 is a diagram for explaining the spread of excreta in the absorbent sheet for pets having continuous recesses.
Figure 6:
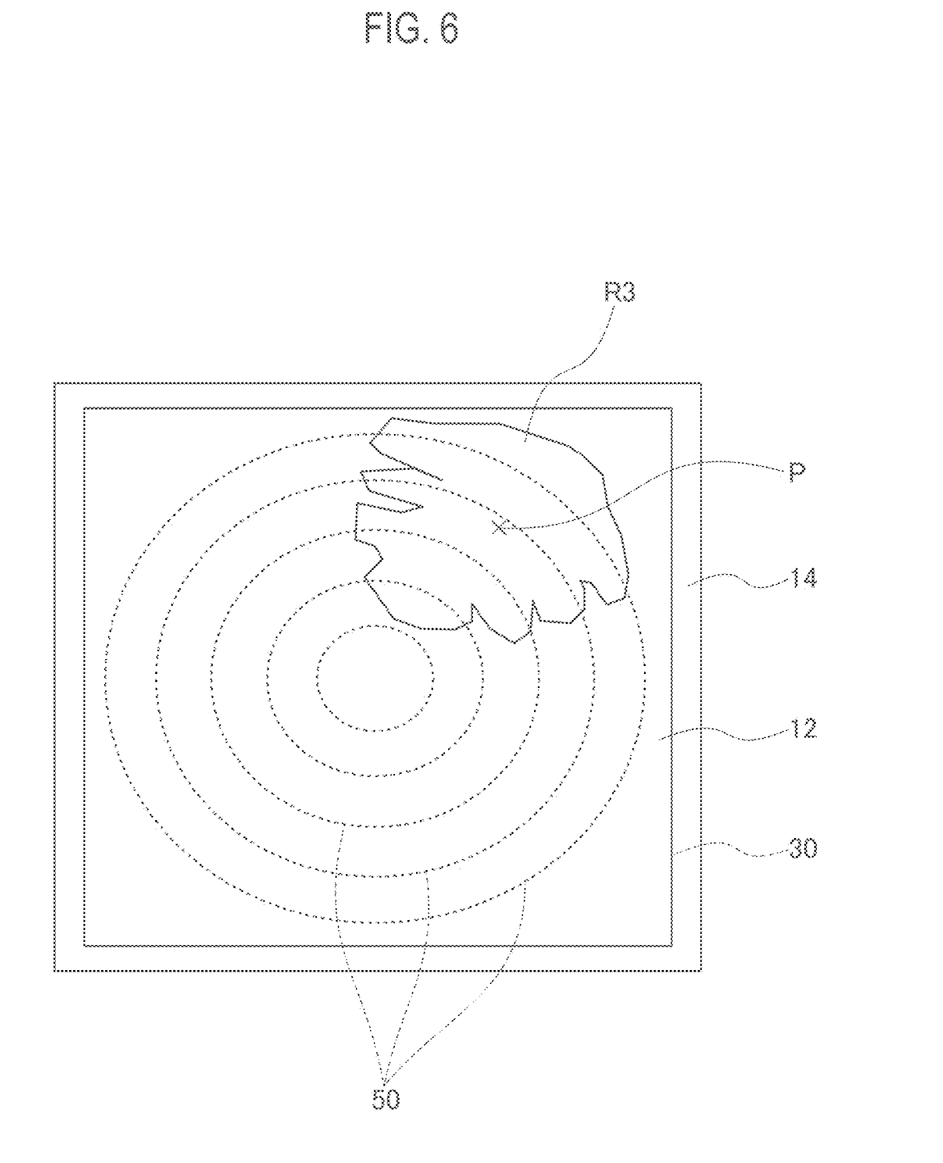
FIG. 6 is a diagram for explaining the spread of excreta in the absorbent sheet for pets having intermittent recesses.

Next, how the excreta spread in the absorbent sheet for pets will be described with reference to FIGS. 4 to 6. FIG. 4 shows an example of an absorbent sheet for pets according to a comparative example having no top recess. FIG. 5 shows an example of the absorbent sheet for pets having the continuous top recesses 50. FIG. 6 shows an example of the absorbent sheet for pets having the intermittent top recesses 50.

In the absorbent sheet for pets according to the comparative example having no top recess, excreta such as urine spread outward in a generally circular shape around the excretion point P (see region R1 in FIG. 4). On the other hand, in the absorbent sheet for pets having the top recesses 50, the pet excreta easily diffuses along the line IL formed by the top recesses 50. Since the line IL formed by the top recesses 50 has a curved portion that does not branch, the excreta does not diffuse linearly from the point P where the pet has performed the excretion action as shown in Patent Literature 1, but diffuses while turning at the curved portion. Therefore, the excreta do not spread linearly toward the end of the sheet from the point P where the excretion action is performed, but is bent for the curved portion (see regions R2 and R3 in FIGS. 5 and 6). As a result, it is possible to prevent the excreta from reaching a point far away from the excretion point P, and it is possible to leave the region which is not polluted with the excreta. As a result, it is easy for the absorbent sheet for pets to withstand the excretion action a plurality of times.

Preferably, the top recesses 50 do not form a continuous line but forms an intermittent line as shown in FIG. 6. When the top recesses 50 form an intermittent line, that is, is provided intermittently, the time required for excreta to move between the top recesses 50 increases. As a result, the speed of diffusion of excreta can be moderately suppressed, and excessive diffusion of excreta can be further suppressed (see region R3 in FIG. 6).

Note that the curved portion of the line IL formed by the top recesses 50 preferably occupies 50% or more of the entire line IL. Specifically, when the top recesses 50 form a continuous line, the length of the curved portion relative to the entire length of the line IL may be 50% or more. When the top recesses 50 form an intermittent line, the ratio of the number of dot shaped top recesses 50 located at the inflection point of the imaginary line to the total number of dot embosses constituting the imaginary line may be 50% or more. As a result, since most of the line IL formed by the top recesses 50 is a curved portion, a line connecting two points on the absorbent sheet for pets 10 are significantly longer than the shortest distance (linear distance). Therefore, it is possible to further suppress the excreta from spreading excessively.

When the top recesses 50 form the intermittent line IL, it is more preferable that the top recesses 51 and 52 which have different depths be located in a line along the line IL. That is, the top recesses 50 may include a first recess 51 and a second recess 52 that is shallower than the first recess 51.

The first recesses 51 and the second recesses 52 may be alternately arranged along the line IL.

The top recesses 51, 52 having different depths are arranged along the line IL, so that it takes time for excreta to move from the deep first recess 51 to the shallow second recess 52. Therefore, the speed of diffusion of excreta along the line IL formed by the top recesses can be moderately suppressed, and excessive diffusion of excreta can be further suppressed.

Again, referring to FIG. 3, a more preferable pattern of the top recesses 50 will be described. The portion along the radial direction R extending outward of the center O of the topsheet 12 (the portion denoted by reference symbol Re in FIG. 3) of the line IL formed by the top recesses 50 is preferably bent so as to have a component along the direction intersecting the radial direction R. As a result, it is possible to prevent the excreta from diffusing linearly toward the edge portion of the absorbent sheet for pets 10 in the radial direction. As a result, the diffusion of excreta to the edge portion of the absorbent sheet for pets 10 can be suppressed.

Further, at least the absorber 20 may be provided with a back recess 54 that is recessed from the back side to the top side. The back recesses 54 are preferably provided at the same position as the top recesses 50 in the thickness direction. Since the excreta easily diffuse along the top recesses 50 of the absorber 20 on the top side, it is easily absorbed into the absorber 20 from the top recesses 50. The excreta absorbed by the absorber 20 from the top recesses 50 is easily retained at the back recesses 54 provided at the same position as the top recesses 50 in the thickness direction. As a result, the excessive diffusion of the excreta from the top recesses 50 and the back recesses 54 to the outside can be suppressed.

Furthermore, the depth of the back recess 54 is preferably shallower than the depth of the top recess 50. The excreta retained at the back recesses 54 may diffuse widely through the boundary between the absorber 20 and the backsheet 14 due to capillary action. According to this aspect, by making the depth of the back recess 54 shallower than the depth of the top recess 50, it is possible to suppress the excessive amount of excreta retained at the back recess 54, and as a result, it is possible to suppress the amount of excreta that spreads through the boundary between the absorber 20 and the backsheet 14. As a result, the excessive diffusion of the excreta from the top recesses 50 and the back recesses 54 to the outside can be suppressed.

Figure 7:
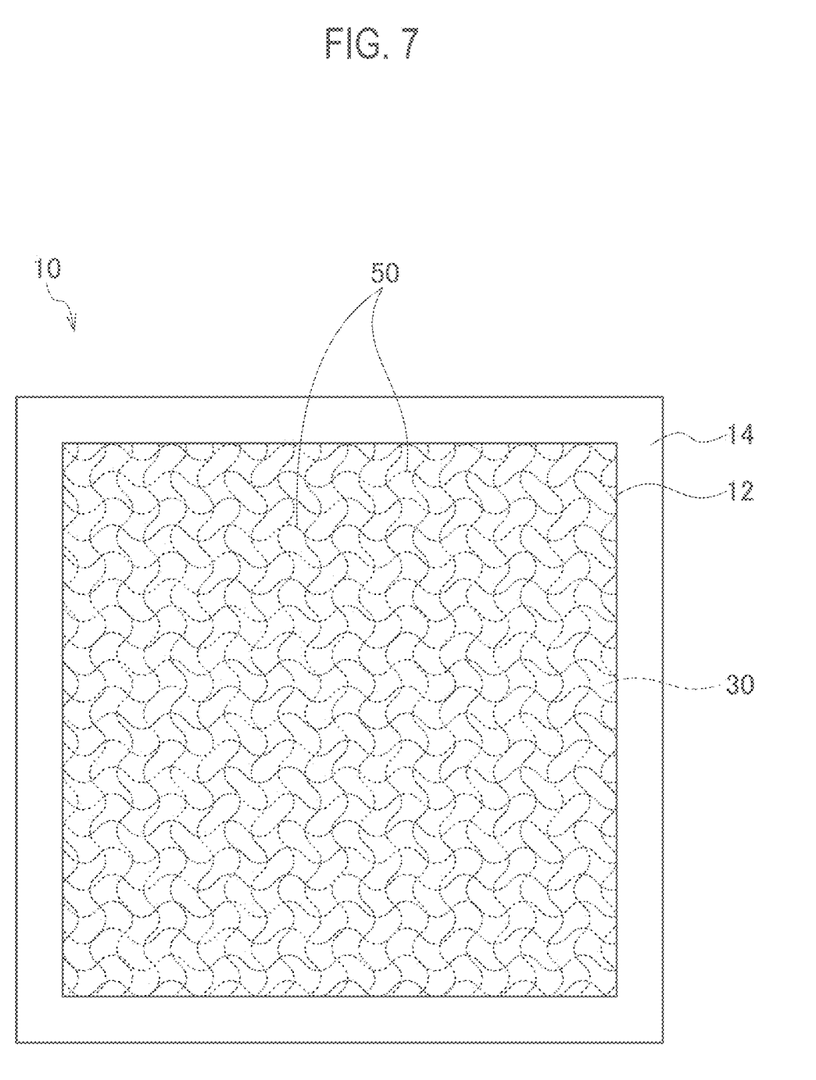
FIG. 7 is a plan view of the absorbent sheet for pets according to a second embodiment.

Next, an absorbent sheet for pets according to another embodiment will be described. FIG. 7 is a plan view of the absorbent sheet for pets according to the second embodiment.

In FIG. 7, the top recesses 50 form the intermittent line IL, but, instead, may form a continuous line. In the present embodiment, the plurality of lines IL formed by the top recesses 50 intersects each other. That is, the line IL has a plurality of branch points. In this way, even when the line IL formed by the top recesses 50 branches, by bending the line IL, the line IL also has a non-branch curved portion.

Even in such an aspect, the excessive diffusion of excreta can be suppressed by the curved portion, of the line IL formed by the top recesses 50, that do not branch.

Figure 8:
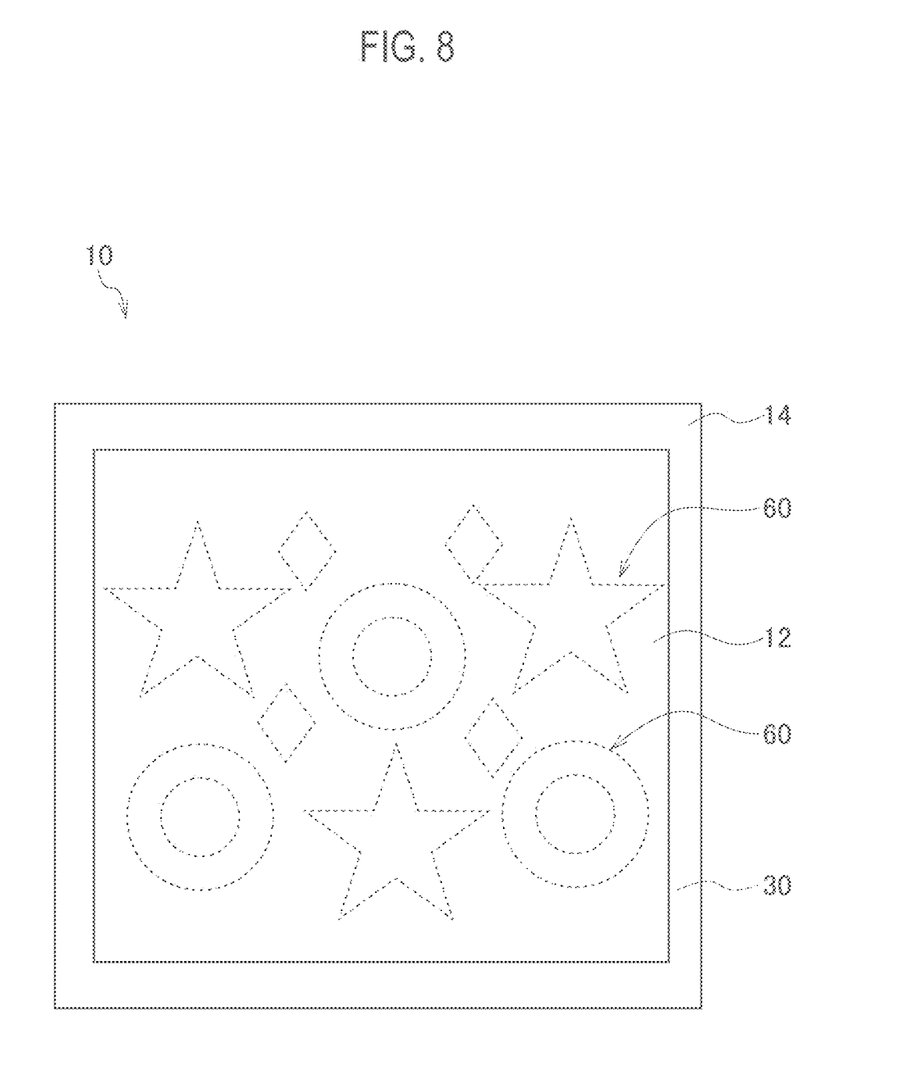
FIG. 8 is a plan view of the absorbent sheet for pets according to a third embodiment.

Next, an absorbent sheet for pets according to another embodiment will be described. FIG. 8 is a plan view of the absorbent sheet for pets according to the third embodiment.

In FIG. 8, the top recesses 50 form an intermittent line, but, instead, may form a continuous line. In the present embodiment, the line IL formed by the top recesses 50 forms a plurality of figures 60 separated from each other. As a result, the excreta locally diffuse on the point where the excretion action is performed or in the figure 60 close to the point and the region in the vicinity thereof. Therefore, excessive diffusion of excreta can be further suppressed.

It is preferable that the figure 60 formed by the top recesses 50 substantially or completely encloses the region within the figure 60. Here, "substantially enclose" means that the line IL constituting the figure 60 exists in all directions when viewed from a certain point in the figure 60. For example, the spiral figure 60 substantially encloses the region within the figure 60. Further, "completely enclose" means that the line IL formed by the top recesses 50 form a closed curve. For example, a circular, polygonal, or star-shaped figure 60 completely encloses a region within the figure 60.

When the excreta reaches the point where the excretion action is performed or the top recesses that form the figure 60 close to the point, the excreta mainly diffuses along the line IL that substantially or completely encloses a region within the figure 60. The excreta diffused in this way gradually diffuse from the line IL to the inner region and the outer region of the figure 60. As a result, the excreta locally diffuse on the point where the excretion action is performed or in the figure 60 close to the point and the region in the vicinity thereof. As a result, excessive diffusion of excreta can be further suppressed.

As mentioned above, although the present invention is explained in detail using the above-mentioned embodiments, it will be apparent to those skilled in the art that the present invention is not limited to the embodiments described herein. The present invention can be implemented as modifications and changes without departing from the spirit and scope of the present invention defined by the description of the claims. Accordingly, the description of the present specification is for the purpose of illustration and is not intended to limit the present invention in any way.

In the above embodiment, the embodiment in which the top recesses 50 form a continuous or intermittent line is described in detail. However, instead of this, the back recesses 54 may form a continuous or intermittent line. In this case, the continuous or intermittent line formed by the back recesses 54 may have a curved portion that does not branch as described above. That is, the back recesses 54 may be formed in the same manner as the top recesses 50 described in the above-described embodiment. Even in this case, the excreta can be prevented from reaching further away from the excretion point and can easily withstand the excretion action a plurality of times. The back recesses 54 can contribute to prevention of diffusion of excreta after being absorbed by the absorber.

The entire contents of Japanese Patent Application No. 2017-118115 filed on Jun. 15, 2017 and Japanese Patent Application No. 2017-202014 filed on Oct. 18, 2017 are incorporated by reference herein.

INDUSTRIAL APPLICABILITY

According to the above aspect, the absorbent sheet for pets which can suppress the spread of the excreta of a pet and can withstand the excretion action a plurality of times can be provided.

REFERENCE SIGNS LIST

10: pets
12: topsheet

14: backsheet
20: absorber
30: absorbent core
50: top recess
54: back recess
IL: line formed by the top recess

The invention claimed is:

1. An absorbent sheet for pets comprising:
a topsheet disposed on a top side;
a backsheet disposed on a back side; and
an absorber provided between the topsheet and the backsheet, wherein
a plurality of recesses is formed at least in the absorber,
the plurality of recesses forms continuous lines or an intermittent line,
the line or lines have a curved portion which does not branch,
a portion of the curved portion along a radial direction extending outward from a center of the
topsheet is bent so as to have a component along a direction intersecting the radial direction, and the plurality of the recesses have different depths arranged along the line.

2. The absorbent sheet for pets according to claim 1, wherein the plurality of recesses forms a spiral figure.

3. The absorbent sheet for pets according to claim 2, wherein the plurality of recesses forms an intermittent line.

4. The absorbent sheet for pets according to claim 2, wherein the plurality of recesses form lines-forming the lines form a plurality of figures separated from each other.

5. The absorbent sheet for pets according to claim 2, wherein the plurality of recesses form lines forming a plurality of figures, and each of the figures formed by the recesses substantially or completely encloses a region within the each figure.

6. The absorbent sheet for pets according to claim 2, wherein the plurality of recesses includes a top recess that is recessed in a direction from the top side toward the back side.

7. The absorbent sheet for pets according to claim 2, wherein the plurality of recesses includes a back recess that is recessed in a direction from the back side toward the top side.

8. The absorbent sheet for pets according to claim 2, wherein
the plurality of recesses includes a top recess that is recessed in the direction from the top side toward
the back side and a back recess that is recessed in the direction from the back side toward the top side, and
the back recess is provided at a position same as a position of the top recess in a thickness direction.

9. The absorbent sheet for pets according to claim 2, wherein the plurality of recesses is formed by an embossed portion obtained by compressing the absorber.

10. The absorbent sheet for pets according to claim 1, wherein the plurality of recesses form lines forming a plurality of figures separated from each other.

11. The absorbent sheet for pets according to claim 1, wherein the plurality of recesses form lines forming a plurality of figures, and each of the figures formed by the plurality of recesses substantially or completely encloses a region within the each figure.

12. The absorbent sheet for pets according to claim 1, wherein the plurality of recesses includes a top recess that is recessed in a direction from the top side toward the back side.

13. The absorbent sheet for pets according to claim 1, wherein the plurality of recesses includes a back recess that is recessed in a direction from the back side toward the top side.

14. The absorbent sheet for pets according to claim 1, wherein
the plurality of recesses includes a top recess that is recessed in the direction from the top side toward
the back side and a back recess that is recessed in the direction from the back side toward the top side, and
the back recess is provided at a position same as a position of the top recess in a thickness direction.

15. The absorbent sheet for pets according to claim 14, wherein a depth of the back recess is shallower than a depth of the top recess.

16. The absorbent sheet for pets according to claim 1, wherein the plurality of recesses is formed by an embossed portion obtained by compressing the absorber.

17. The absorbent sheet for pets according to claim 1 wherein the curved portion occupies 50% or more of the entire line.

* * * * *